(12) United States Patent
Zhang

(10) Patent No.: US 11,034,656 B2
(45) Date of Patent: Jun. 15, 2021

(54) MALEATE SALTS OF (E)-N-(3-CYANO-7-ETHOXY-4-((4-PHENOXYPHENYL)AMINO) QUINOLIN-6-YL)-4-(DIMETHYLAMINO) BUT-2-ENAMIDE AND CRYSTALLINE FORMS THEREOF

(71) Applicant: TELIGENE LTD, Suzhou (CN)

(72) Inventor: Dawei Zhang, Thousand Oaks, CA (US)

(73) Assignee: Teligene Ltd., Suzhou (CN)

( * ) Notice: Subject to any disclaimer, the term of this patent is extended or adjusted under 35 U.S.C. 154(b) by 0 days.

(21) Appl. No.: 16/765,473

(22) PCT Filed: Nov. 20, 2018

(86) PCT No.: PCT/CN2018/116484
§ 371 (c)(1),
(2) Date: May 19, 2020

(87) PCT Pub. No.: WO2019/096327
PCT Pub. Date: May 23, 2019

(65) Prior Publication Data
US 2020/0290968 A1 Sep. 17, 2020

Related U.S. Application Data

(60) Provisional application No. 62/707,816, filed on Nov. 20, 2017.

(51) Int. Cl.
*C07D 215/54* (2006.01)

(52) U.S. Cl.
CPC ........ *C07D 215/54* (2013.01); *C07B 2200/13* (2013.01)

(58) Field of Classification Search
CPC .......................... C07D 215/54; C07B 2200/13
See application file for complete search history.

(56) References Cited

U.S. PATENT DOCUMENTS

| 2006/0270668 | A1 | 11/2006 | Chew et al. |
| 2009/0176827 | A1 | 7/2009 | Lu et al. |
| 2015/0057312 | A1* | 2/2015 | Zhang ..................... A61P 35/00 514/313 |
| 2018/0265495 | A1 | 9/2018 | Chen et al. |

FOREIGN PATENT DOCUMENTS

CN 104513200 A 4/2015

* cited by examiner

*Primary Examiner* — Timothy R Rozof
(74) *Attorney, Agent, or Firm* — Feng Tian

(57) ABSTRACT

The present application relates to maleate salts of (E)-N-{4-[3-chloro-4-(2-pyridinylmethoxy)aniline]-3-cyano-7-ethoxy-6-quinolinyl}-4-(dimethylamino)-2-butenamide, crystalline forms thereof, to processes for its preparation, to pharmaceutical compositions comprising it and to its use in the control of disorders.

20 Claims, 9 Drawing Sheets

MALEATE SALTS OF (E)-N-(3-CYANO-7-ETHOXY-4-((4-PHENOXYPHENYL)AMINO) QUINOLIN-6-YL)-4-(DIMETHYLAMINO) BUT-2-ENAMIDE AND CRYSTALLINE FORMS THEREOF

RELATED APPLICATION

The present application claims the benefit of U.S. Provisional Patent Application No. 62/707,816, filed on Nov. 20, 2017, which is incorporated herein by reference in its entirety.

FIELD OF THE INVENTION

The present application relates to maleate salts of (E)-N-(3-cyano-7-ethoxy-4-((4-phenoxyphenyl)amino)quinolin-6-yl)-4-(dimethylamino)but-2-enamide, crystalline forms thereof, methods of preparing the salts, associated compounds, pharmaceutical compositions containing the maleate salt, and methods for their use. Maleate salts of (E)-N-(3-cyano-7-ethoxy-4-((4-phenoxyphenyl)amino)quinolin-6-yl)-4-(dimethylamino) but-2-enamide are useful in the treatment of cancer.

BACKGROUND OF THE INVENTION (E)-N-(3-cyano-7-ethoxy-4-((4-phenoxyphenyl)amino)quinolin-6-yl)-4-(dimethylamino)but-2-enamide is mentioned in WO2013152135 and corresponds to the compound of the Formula I:

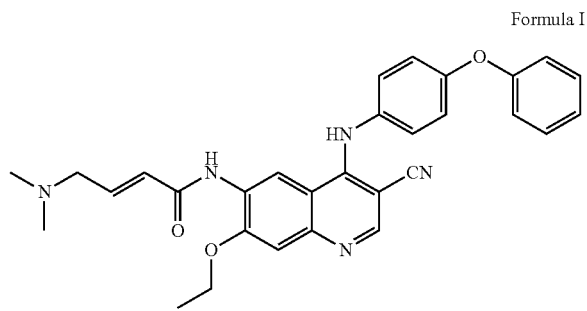 [SMILES: CCOc1cc2ncc(C#N)c(Nc3ccc(Oc4ccccc4)cc3)c2cc1NC(=O)/C=C/CN(C)C]

Formula I

Compounds derived from 3-cyanoquinoline have been shown to have anti-tumor activity, which may make them useful as chemotherapeutic agents in treating various cancers, including but not limited to, pancreatic cancer, melanoma, lymphatic cancer, parotid tumors, Barrett's esophagus, esophageal carcinomas, head and neck tumors, ovarian cancer, breast cancer, epidermoid tumors, cancers of major organs, such as kidney, bladder, larynx, stomach, and lung, colonic polyps and colorectal cancer and prostate cancer. Examples of compounds derived from 3-cyanoquinoline are disclosed and shown to possess anti-tumor activity in many literatures. One limitation of certain 3-cyanoquinoline compounds is that they are not water soluble in a free base form.

The crystalline form of a particular drug as a salt, a hydrate and/or any polymorph thereof is often one important determinant of the drug's ease of preparation, stability, water solubility, storage stability, ease of formulation and in-vivo pharmacology. It is possible that one crystalline form is preferable over another where certain aspects such as ease of preparation, stability, water solubility and/or superior pharmacokinetics are deemed to be critical. Crystalline forms of (E)-N-(3-cyano-7-ethoxy-4-((4-phenoxyphenyl)amino)quinolin-6-yl)-4-(dimethylamino)but-2-enamide salts that possess a higher degree of water solubility than the free base but are stable fulfill an unmet need for stable, crystalline, water-soluble forms of substituted 3-cyanoquinoline compounds that selectively inhibit kinase activity, which in turn inhibit cell proliferation and tumorgenesis.

SUMMARY OF THE INVENTION

In one aspect, the present application provides a maleate salt of (E)-N-(3-cyano-7-ethoxy-4-((4-phenoxyphenyl)amino)quinolin-6-yl)-4-(dimethylamino)but-2-enamide. In a particular aspect, the present application provides (E)-N-(3-cyano-7-ethoxy-4-((4-phenoxyphenyl)amino)quinolin-6-yl)-4-(dimethylamino)but-2-enamide maleate monohydrate. In another particular aspect, the present application provides crystalline forms of (E)-N-(3-cyano-7-ethoxy-4-((4-phenoxyphenyl)amino)quinolin-6-yl)-4-(dimethylamino)but-2-enamide maleate, which have been isolated and characterized as: an anhydrous form, a monohydrate form, and a mixture of the anhydrous and the monohydrate forms (referred to as a partial hydrate form).

In another aspect, the application provides methods for the preparing ((E)-N-(3-cyano-7-ethoxy-4-((4-phenoxyphenyl)amino)quinolin-6-yl)-4-(dimethylamino)but-2-enamide as a maleate salt including monohydrate thereof.

In another aspect, the application provides pharmaceutical compositions comprising a maleate salt of ((E)-N-(3-cyano-7-ethoxy-4-((4-phenoxyphenyl)amino)quinolin-6-yl)-4-(dimethylamino)but-2-enamide and monohydrate thereof.

In another aspect, the application provides methods for preventing or inhibiting cancer in a subject comprising administrating the subject a therapeutically effective amount of a maleate salt of ((E)-N-(3-cyano-7-ethoxy-4-((4-phenoxyphenyl)amino)quinolin-6-yl)-4-(dimethylamino)but-2-enamide and monohydrate thereof.

DETAILED DESCRIPTION OF THE INVENTION (E)-N-(3-cyano-7-ethoxy-4-((4-phenoxyphenyl)amino)quinolin-6-yl)-4-(dimethylamino)but-2-enamide is an irreversible inhibitor to BTK and Her-2 (also known as Erb-2 or neu) kinase, a member of the epidermal growth factor receptor (EGFR) family. EGFR family members have been implicated in tumorigenesis and associated with poor prognosis in tumor types in humans. The structure of the (E)-N-(3-cyano-7-ethoxy-4-((4-phenoxyphenyl)amino)quinolin-6-yl)-4-(dimethylamino)but-2-enamide in the form of a free base is shown below:

Formula I

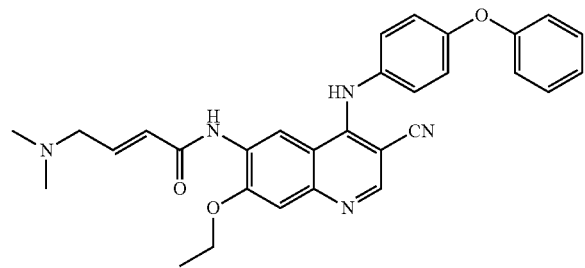 [SMILES: CCOc1cc2ncc(C#N)c(Nc3ccc(Oc4ccccc4)cc3)c2cc1NC(=O)/C=C/CN(C)C]

The compound (E)-N-(3-cyano-7-ethoxy-4-((4-phenoxyphenyl)amino)quinolin-6-yl)-4-(dimethylamino)but-2-enamide in the form of a free base is described in WO2013152135. There is a need for a form of this compound with improved physicochemical properties, and better bioavailability.

In some embodiments, the application provides a maleate salt of (E)-N-(3-cyano-7-ethoxy-4-((4-phenoxyphenyl)amino)quinolin-6-yl)-4-(dimethylamino)but-2-enamide.

In some embodiments, the application provides a maleate salt of (E)-N-(3-cyano-7-ethoxy-4-((4-phenoxyphenyl)amino)quinolin-6-yl)-4-(dimethylamino)but-2-enamide which is a 1:1 molar ratio of (E)-N-(3-cyano-7-ethoxy-4-((4-phenoxyphenyl)amino)quinolin-6-yl)-4-(dimethylamino)but-2-enamide to maleic acid.

In some embodiments, the present application provides (E)-N-(3-cyano-7-ethoxy-4-((4-phenoxyphenyl)amino)quinolin-6-yl)-4-(dimethylamino)but-2-enamide maleate monohydrate.

In some embodiments, the present application provides crystalline forms of (E)-N-(3-cyano-7-ethoxy-4-((4-phenoxyphenyl)amino)quinolin-6-yl)-4-(dimethylamino)but-2-enamide maleate, which have been isolated and characterized as: an anhydrous form, a monohydrate form, and a mixture of the anhydrous and the monohydrate forms (referred to as a partial hydrate form).

Figure 3:
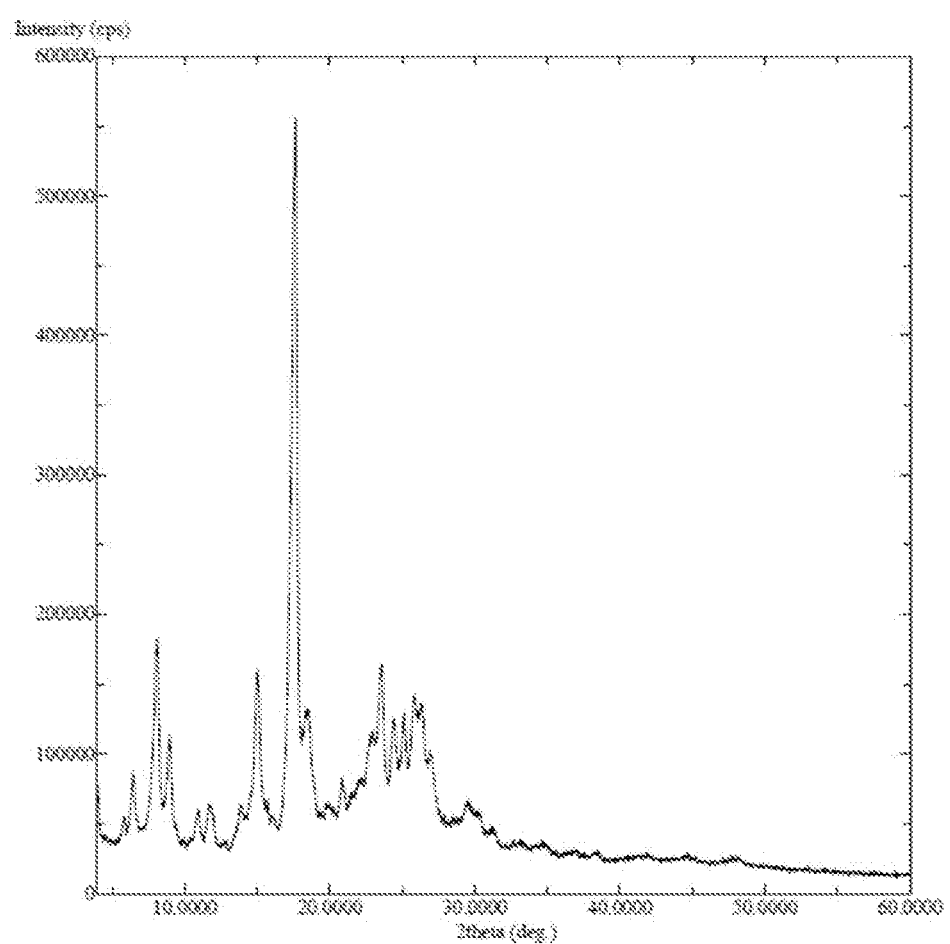
FIG. 3: PXRD of (E)-N-{4-[3-chloro-4-(2-pyridinylmethoxy)aniline]-3-cyano-7-ethoxy-6-quinolinyl}-4-(dimethylamino)-2-butenamide maleate salt crystalline (Form II)
Figure 4:
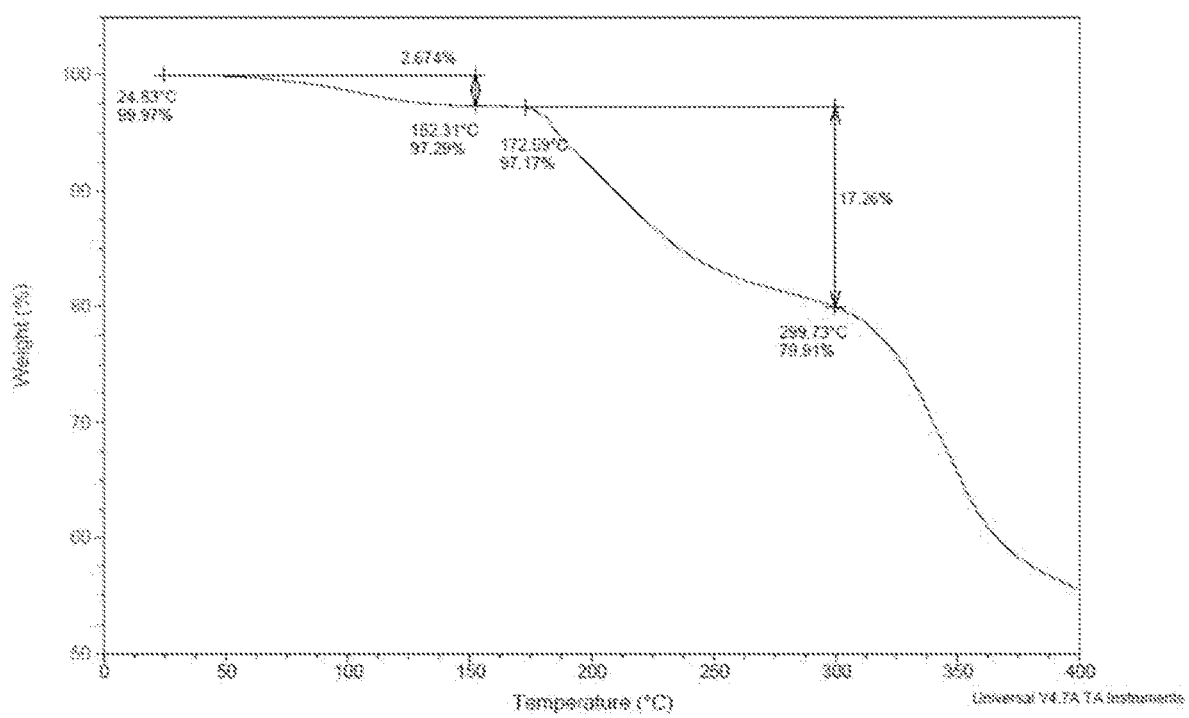
FIG. 4: TGA thermogram of (E)-N-{4-[3-chloro-4-(2-pyridinylmethoxy)aniline]-3-cyano-7-ethoxy-6-quinolinyl}-4-(dimethylamino)-2-butenamide maleate salt monohydrate.

In some embodiments, the present application provides a crystalline form (Form II) of (E)-N-(3-cyano-7-ethoxy-4-((4-phenoxyphenyl)amino)quinolin-6-yl)-4-(dimethylamino)but-2-enamide maleate, which is characterized by its powder X-ray diffraction (PXRD) pattern having characteristic peaks at about 8.1, 15.0, 17.6, and 23.6 degree of 2θ (±0.2). The crystalline Form II of the application is further characterized by its PXRD having additional peaks at about 9.0, 18.5, 22.7, 23.0, and 25.1. The crystalline Form II of the application is characterized by its PXRD having essentially the same as shown in FIG. 3.

Figure 1:
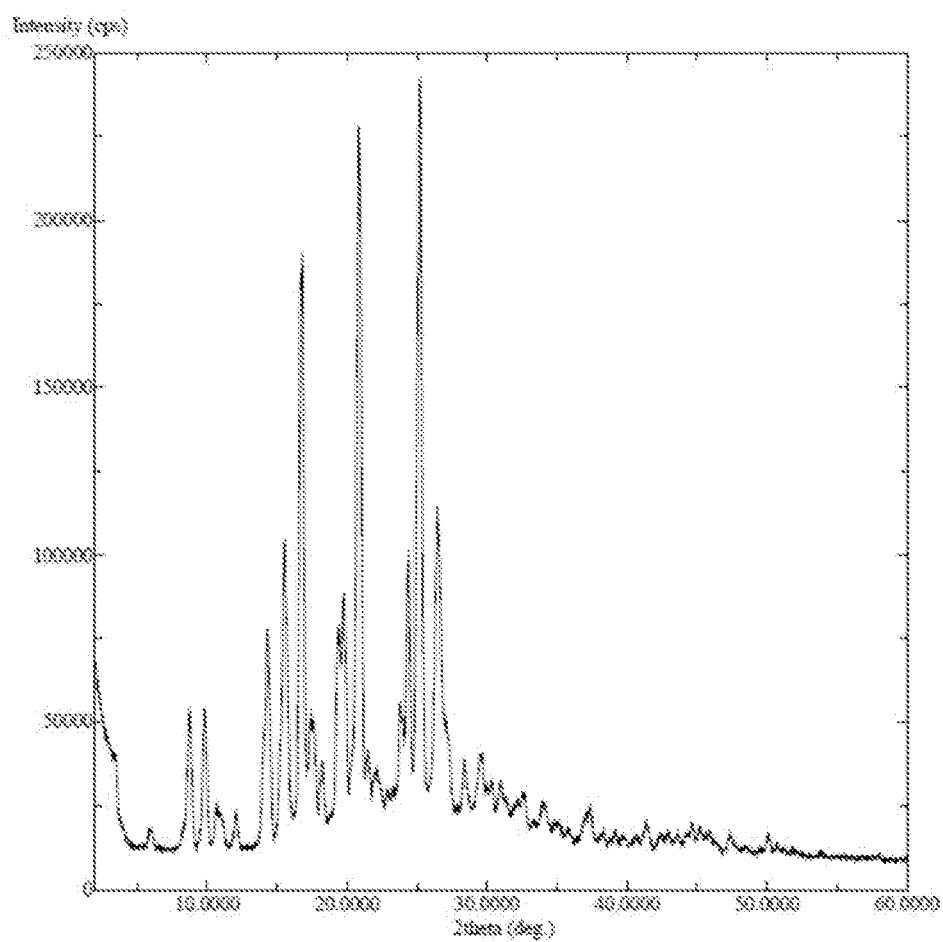
FIG. 1: PXRD of (E)-N-{4-[3-chloro-4-(2-pyridinylmethoxy)aniline]-3-cyano-7-ethoxy-6-quinolinyl}-4-(dimethylamino)-2-butenamide maleate salt monohydrate crystalline (Form I)

In some embodiments, the present application provides a crystalline form (Form I) of (E)-N-(3-cyano-7-ethoxy-4-((4-phenoxyphenyl)amino)quinolin-6-yl)-4-(dimethylamino)but-2-enamide maleate monohydrate, which is characterized by its powder X-ray diffraction (PXRD) pattern having characteristic peaks at about 15.5, 16.8, 20.9, 24.4, 25.2 and 26.5 degree of 2θ (±0.2). The crystalline Form I of the application is further characterized by its PXRD having additional peaks at about 8.7, 9.8, 14.3, 17.4, 19.3, 19.8, and 23.8. The crystalline Form I of the application is characterized by its PXRD having essentially the same as shown in FIG. 1.

Figure 2:
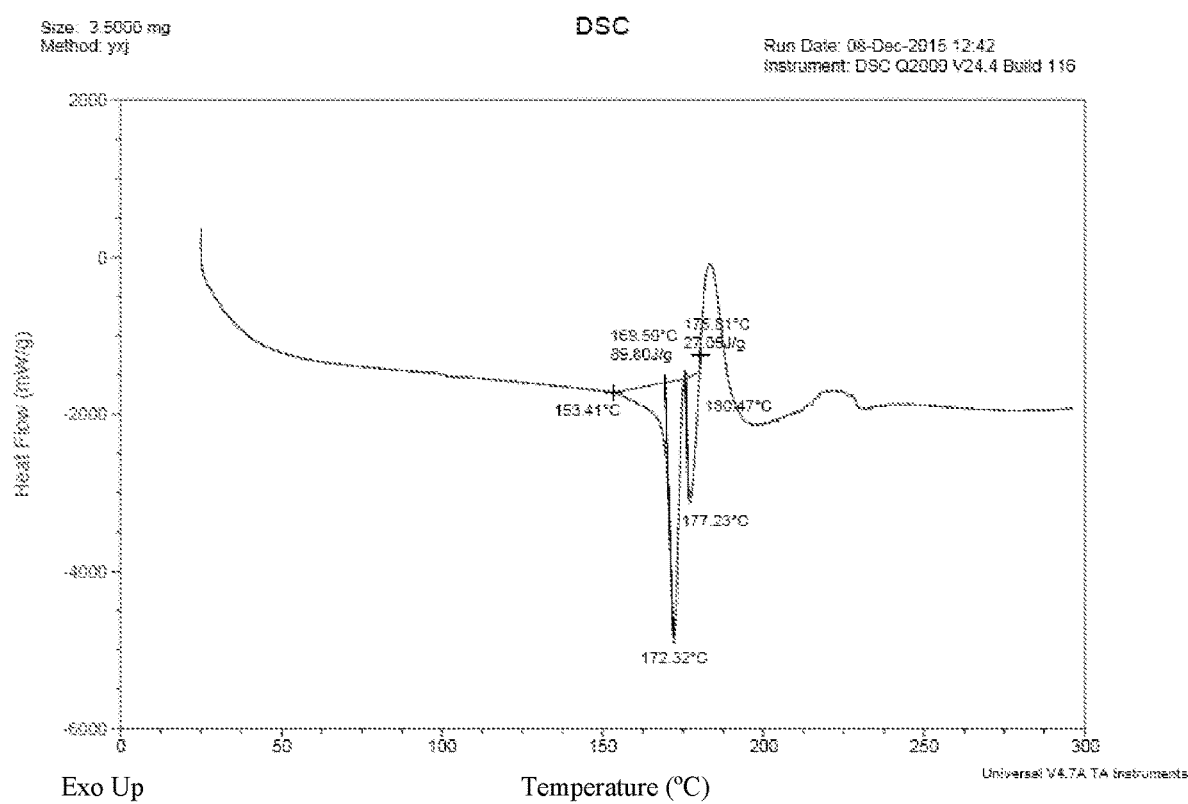
FIG. 2: DSC thermogram of (E)-N-{4-[3-chloro-4-(2-pyridinylmethoxy)aniline]-3-cyano-7-ethoxy-6-quinolinyl}-4-(dimethylamino)-2-butenamide maleate salt monohydrate.

In some embodiments, the present application provides a crystalline form (Form I) of (E)-N-(3-cyano-7-ethoxy-4-((4-phenoxyphenyl)amino)quinolin-6-yl)-4-(dimethylamino)but-2-enamide maleate monohydrate, which is characterized by its differential scanning calorimetry (DSC) thermogram having two endothermic peaks between about 153° C. and about 180° C. The crystalline Form I of the application is characterized by its DSC thermogram having essentially the same as shown in FIG. 2.

Figure 5:
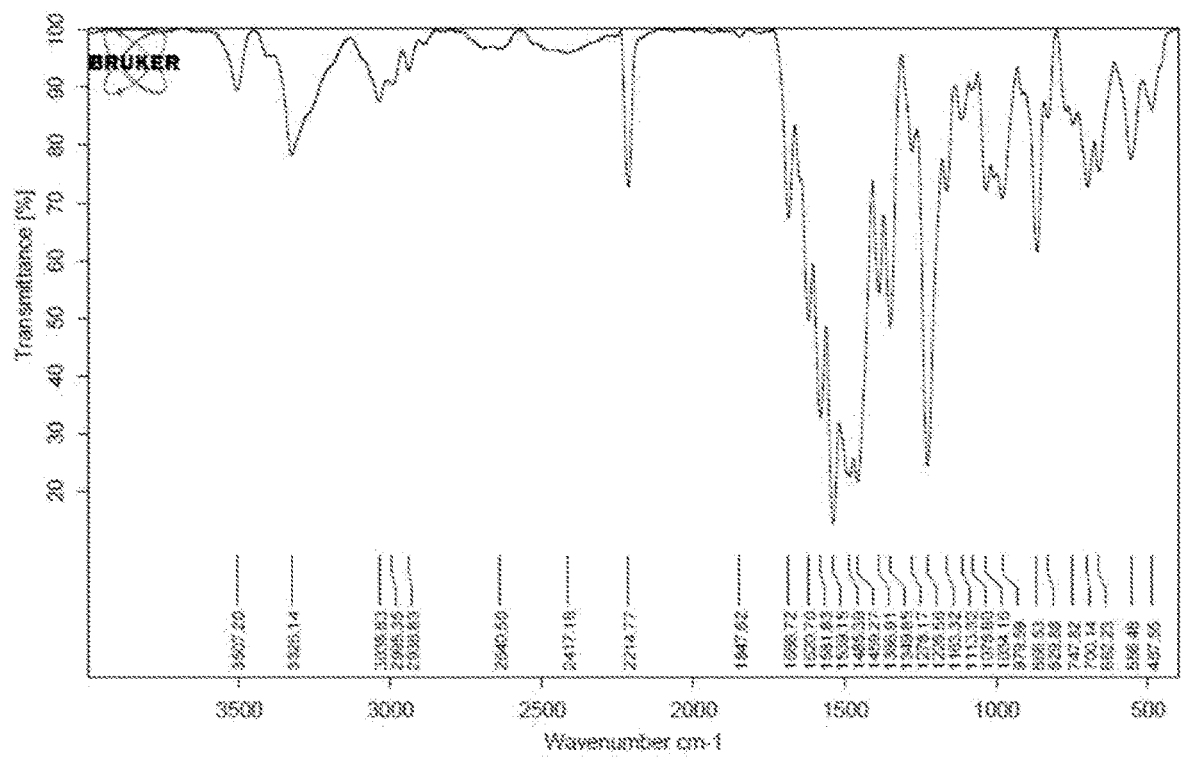
FIG. 5: IR spectrum of (E)-N-{4-[3-chloro-4-(2-pyridinylmethoxy)aniline]-3-cyano-7-ethoxy-6-quinolinyl}-4-(dimethylamino)-2-butenamide maleate salt monohydrate.

In some embodiments, the present application provides a crystalline form (Form I) of (E)-N-(3-cyano-7-ethoxy-4-((4-phenoxyphenyl)amino)quinolin-6-yl)-4-(dimethylamino)but-2-enamide maleate monohydrate, which is characterized by its infrared spectroscopy (IR) comprising one or more peaks at about 3507.20, 3326.14, 3036.83, 2995.35, 2938.83, 2640.50, 2417.18, 2214.77, 1847.62, 1686.72, 1620.70, 1581.83, 1539.15, 1485.39, 1459.27, 1386.91, 1349.85, 1278.17, 1226.56, 1163.32, 1113.32, 1078.80, 1034.16, 979.59, 866.53, 829.88, 747.82, 700.14, 662.23, 556.48, and 487.55 cm$^{-1}$. The crystalline Form I of the application is characterized by its IR having essentially the same as shown in FIG. 5.

In some embodiments, the application provides methods for the preparing a maleate salt of ((E)-N-(3-cyano-7-ethoxy-4-((4-phenoxyphenyl)amino)quinolin-6-yl)-4-(dimethylamino)but-2-enamide comprising the step of: mixing ((E)-N-(3-cyano-7-ethoxy-4-((4-phenoxyphenyl)amino)quinolin-6-yl)-4-(dimethylamino)but-2-enamide and maleic acid in a water-alcohol solution or an alcohol solution at an elevated temperature. The methods further include the steps of: cooling said solution to precipitate maleate salt, and filtering and drying.

In some embodiments, the said alcohol is selected from one or more of methanol, ethanol, n-propanol, and isopropanol.

In some embodiments, the application provides a method of preparing (E)-N-(3-cyano-7-ethoxy-4-((4-phenoxyphenyl)amino)quinolin-6-yl)-4-(dimethylamino)but-2-enamide maleate monohydrate comprising the steps selected from the group consisting of: a. dissolving anhydrous (E)-N-(3-cyano-7-ethoxy-4-((4-phenoxyphenyl)amino)quinolin-6-yl)-4-(dimethylamino)but-2-enamide maleate with an organic solvent, adding water, and filtering; b. dissolving anhydrous (E)-N-(3-cyano-7-ethoxy-4-((4-phenoxyphenyl)amino)quinolin-6-yl)-4-(dimethylamino)but-2-enamide maleate with an organic solvent, adding a solution of a second organic solvent and water, and filtering; c. dissolving anhydrous (E)-N-(3-cyano-7-ethoxy-4-((4-phenoxyphenyl)amino)quinolin-6-yl)-4-(dimethylamino)but-2-enamide maleate with an organic solvent containing water, and filtering; and d. reslurrying anhydrous (E)-N-(3-cyano-7- ethoxy-4-((4-phenoxyphenyl)amino)quinolin-6-yl)-4-(dimethylamino)but-2-enamide maleate with an organic solvent containing water for a period of days, and filtering; e. dissolving anhydrous ((E)-N-(3-cyano-7-ethoxy-4-((4-phenoxyphenyl)amino)quinolin-6-yl)-4-(dimethylamino)but-2-enamide maleate with water, and filtering.

In some embodiments, the said organic solvent is selected from one or more of methanol, ethanol, n-propanol, and isopropanol In some embodiments, the application provides methods for preventing or inhibiting cancer in a subject comprising administrating the subject a therapeutically effective amount of a maleate salt of ((E)-N-(3-cyano-7-ethoxy-4-((4-phenoxyphenyl)amino)quinolin-6-yl)-4-(dimethylamino)but-2-enamide and monohydrate thereof. The maleate salts and crystalline forms of the present application are useful for preventing, treating, or inhibiting inflammation or cancer by administering a therapeutically-effective amount of compound (E)-N-(3-cyano-7-ethoxy-4-((4-phenoxyphenyl)amino)quinolin-6-yl)-4-(dimethylamino)but-2-enamide maleate or crystalline forms thereof to a subject. The subject may be a mammal, and more specifically, a human. The maleate salt may be administered in its anhydrous form, monohydrate form or partially hydrated form. Crystalline forms of the maleate salts of the present application are useful for preparing pharmaceutical compositions for the inhibition of BTK and/or HER-2 kinase activity, effective amount of compound (E)-N-(3-cyano-7-ethoxy-4-((4-phenoxyphenyl)amino)quinolin-6-yl)-4-(dimethylamino)but-2-enamide maleate and a pharmaceutically acceptable carrier. The pharmaceutical composition may be administered in its anhydrous form, monohydrate form or partially hydrated form.

Pharmaceutical compositions and formulations of the present application may be useful in the treatment of one or more of breast cancer, ovarian cancer, epidermoid tumors, colon cancer, prostate cancer, kidney cancer, bladder cancer, larynx cancer, esophagus cancer, stomach cancer, lung cancer, chronic lymphocytic leukemia, mantle cell lymphoma, diffuse large B-cell lymphoma, or multiple myeloma. According to one embodiment, the maleate salt is particularly useful in the treatment of breast cancer and/or ovarian cancer.

In some embodiments, the application provides pharmaceutical compositions comprising a maleate salt of ((E)-N-(3-cyano-7-ethoxy-4-((4-phenoxyphenyl)amino)quinolin-6-yl)-4-(dimethylamino)but-2-enamide or monohydrate, or crystalline forms thereof.

The pharmaceutical compositions and formulations including maleate salt forms of the application may be administered orally, by intralesional, intraperitoneal, intramuscular or intravenous injection; infusion; liposome-mediated delivery; topical, nasal, anal, vaginal, sublingual, uretheral, transdermal, intrathecal, ocular or otic delivery. One mode of administration for the compound of the application is the unit dose form. Suitable unit dose forms include tablets, capsules and powders in sachets or vials. The crystalline compounds of the present application can be administered orally. Such compounds may be administered from 1 to 6 times a day more usually from 1 to 4 times a day. The effective amount will be known to one of skill in the art; it may also be dependent upon the form of the compound, the mode of administration and the serverity of the condition being treated. One of skill in the art could routinely perform empirical activity tests to determine the bioactivity of the compound in bioassays and thus determine what dosage to administer. However, in general, satisfactory results can be obtained with compounds of the present application when dosed daily in the range of about 0.5 mg/kg to about 1000 mg/kg of body weight, but usually the effective dosage amount is between about 1 mg/kg to about 300 mg/kg per day.

The crystalline forms of maleate salts of the application may be formulated with conventional excipients, such as fillers, disintegrating agents, binders, lubricants, flavoring agents, color additives, and carriers. The carrier may be a diluent, an aerosol, a topical carrier, an aqueous solution, a nonaqueous solution or a solid. The carrier may be a polymer or a toothpaste. A carrier in this application encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules. If administered orally or topically, the crystalline forms of maleate salts of the application may be provided to a subject in different carriers. Typically, such carriers contain excipients such as starch, milk, sugar, certain types of clay, gelatin, stearic acid, talc, vegetable fats or oils, gums, or glycols. Specific carriers are typically selected based upon the desired method of delivery, for example, phosphate buffered saline (PBS) could be used for intravenous or systemic delivery and vegetable fats, creams, salves, ointments or gels may be used for topical delivery. The crystalline forms of maleate salts of the present application may be delivered together with suitable diluents, preservatives, solubilizers, emulsifiers, adjuvants and/or carriers useful in treatment, inhibition or prevention of neoplasm. Such compositions are liquids or lyophilized or otherwise dried formulations and include diluents of various buffer content (for example, TrisHCl, acetate, phosphate), pH and ionic strength, additives such as albumins or gelatin to prevent absorption to surfaces, detergents (for example, TWEEN™ 20, TWEEN™ 80, PLURONIC™ F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multi lamellar vesicles, erythrocyte ghosts, or spheroblasts. Such compositions will influence the physical state, solubility, stability, rate of in vivo release, and rate of in-vivo clearance of the compound or composition. The choice of compositions will depend on the physical and chemical properties of the compound. The crystalline forms of maleate salts of the application also may be delivered locally via a capsule that allows a sustained release of the compound over a period of time. Controlled or sustained release compositions include formulations in lipophilic depots (for example, fatty acids, waxes, oils).

The crystalline forms of maleate salts of the application can also be dosed with other active compounds that would be of benefit to a patient suffering from cancer, for example, other chemo agents or anti-biotics, or in conjunction with radiation therapy. These active compounds can be dosed with the compounds of the present application simultaneously or in sequence. The compounds of the present application can also be formulated to include the other active compound in the same dosage unit, for example both could be contained within one pill, table or capsule. Some of the possible types of active compounds that the compounds of the present application could be used in combination with are mitotic inhibitors, such as taxol and vinblastine, alkylating agents, such as cisplatin and cyclophosamide, antimetabolites, such as 5-fluorouracil and hydroxyurea, DNA intercalators, such as adriamycin and bleomycin, topoisomerase inhibitors, such as etoposide and camptothecin, antiangiogenic agents, such as angiostatin, and antiestrogens, such as tamoxifen. This application will be more fully described in conjunction with the following specific examples, which should not to be construed as limiting the scope of this application. A skilled artisan will be able to re-arrange, combine, modify, or eliminate steps in the exemplified process, depending on process parameters and equipment.

The term "crystalline" as used herein, means having a regularly repeating arrangement of molecules or external face planes. Crystalline forms may differ with respect to thermodynamic stability, physical parameters, x-ray structure and preparation processes.

The term "amorphous" refers to a disordered solid state.

The term "anhydrous" as used herein, means a crystalline form containing less than about 1% (w/w) of adsorbed moisture as determined by standard methods, such as a Karl Fisher analysis.

The term "essentially the same" means that variability typical for a particular method is taken into account. For example, with reference to X-ray diffraction peak positions, the term "essentially the same" means that typical variability in peak position and intensity are taken into account. One skilled in the art will appreciate that the peak positions (2θ) will show some variability, typically as much as ±0.2°. Further, one skilled in the art will appreciate that relative peak intensities will show inter-apparatus variability as well as variability due to degree of crystallinity, preferred orientation, prepared sample surface and other factors known to those skilled in the art and should be taken as qualitative measures only.

Hygroscopicity tests of ((E)-N-(3-cyano-7-ethoxy-4-((4-phenoxyphenyl)amino) quinolin-6-yl)-4-(dimethylamino)but-2-enamide in different acid salts have been carried out by the following method:

Hygroscopicity Test

Step 1:
Take the dry glass weighing bottle which has a plug (outer diameter is 50 mm, high is 15 mm); placed in a suitable 25° C.±1° C. constant temperature dryer (place a saturated solution of ammonium chloride or ammonium sulfate in the lower part) or artificial climate box (set the temperature to 25° C.±1° C. and the relative humidity to 80%±2%) one day before the test, accurately weighting its weight ($m_1$).

Step 2:
Take appropriate amount of the test sample and lay it in the above weighing bottle, the thickness of the test sample is generally 1 mm, accurately weighting its weight ($m_2$).

Step 3:
Open the weighing bottle and place it at the constant temperature and humidity as above-mentioned for 24 hours with its plug.

Step 4:
Accurately weighting its weight ($m_3$), including the weighing bottle and its plug.

Percentage of weight gain=$(m_3-m_2)/(m_2-m_1)*100\%$

| Salt samples | $m_1$ (bottle) | $m_2$ (sample + bottle) | $m_3$ (sample + bottle) | weight gain (%) | Results |
|---|---|---|---|---|---|
| Hydrochloride acid salt | 27.4334 | 27.4799 | 27.5016 | 46.67% | Highly wetting property |
| Citrate salt | 30.5584 | 30.7966 | 30.8610 | 27.04% | Highly wetting property |
| L-malate salt | 27.9296 | 28.4138 | 28.4930 | 16.36% | Highly wetting property |
| Sulphate salt | 28.8232 | 29.0405 | 29.1190 | 36.13% | Highly wetting property |
| Maleate salt | 31.23123 | 31.68383 | 31.68471 | 0.2% | Slightly arthroscopic |

Definition

Deliquesce: Absorb enough water to form liquid;

Highly wetting property: Percentage of weight gain is no less than 15%;

Humidity: Percentage of weight gain is less than 15% but no less than 2%;

Slightly arthroscopic: Percentage of weight gain is less than 2% but no less than 0.2%;

No or almost no arthroscopic: Percentage of weight gain is less than 0.2%.

Salts

Figure 6:
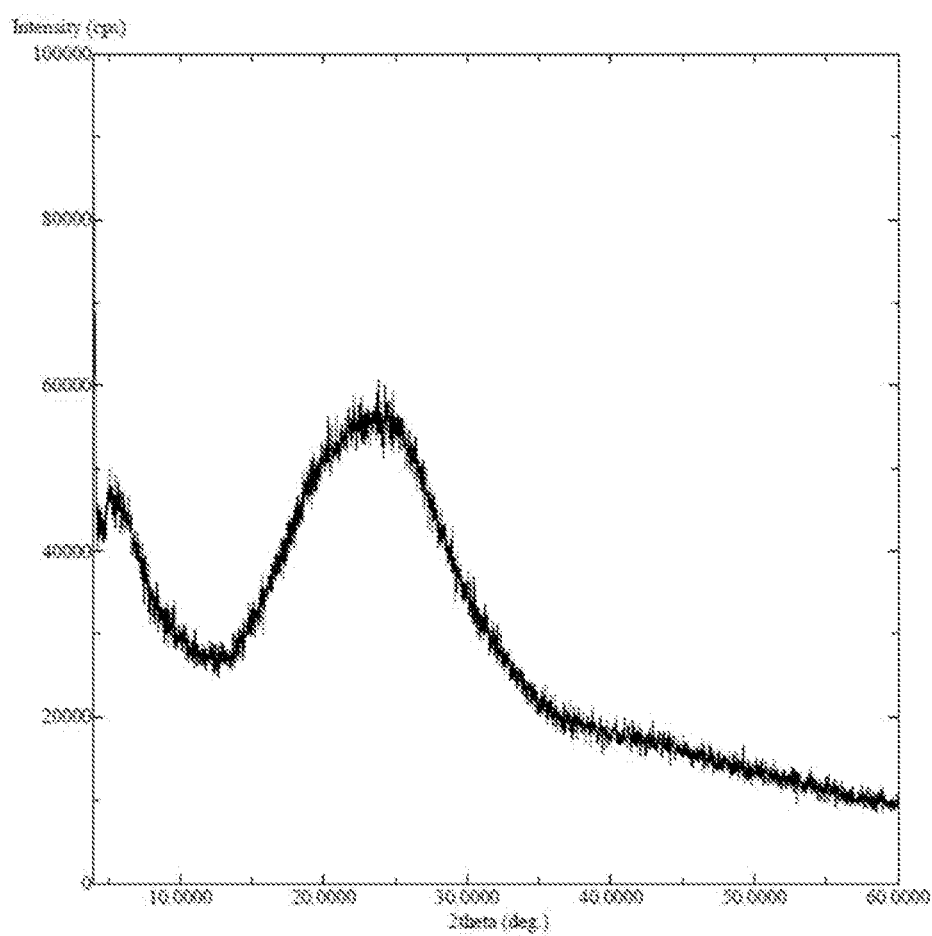
FIG. 6: PXRD of (E)-N-{4-[3-chloro-4-(2-pyridinylmethoxy)aniline]-3-cyano-7-ethoxy-6-quinolinyl}-4-(dimethylamino)-2-butenamide hydrochloride acid salt.
Figure 7:
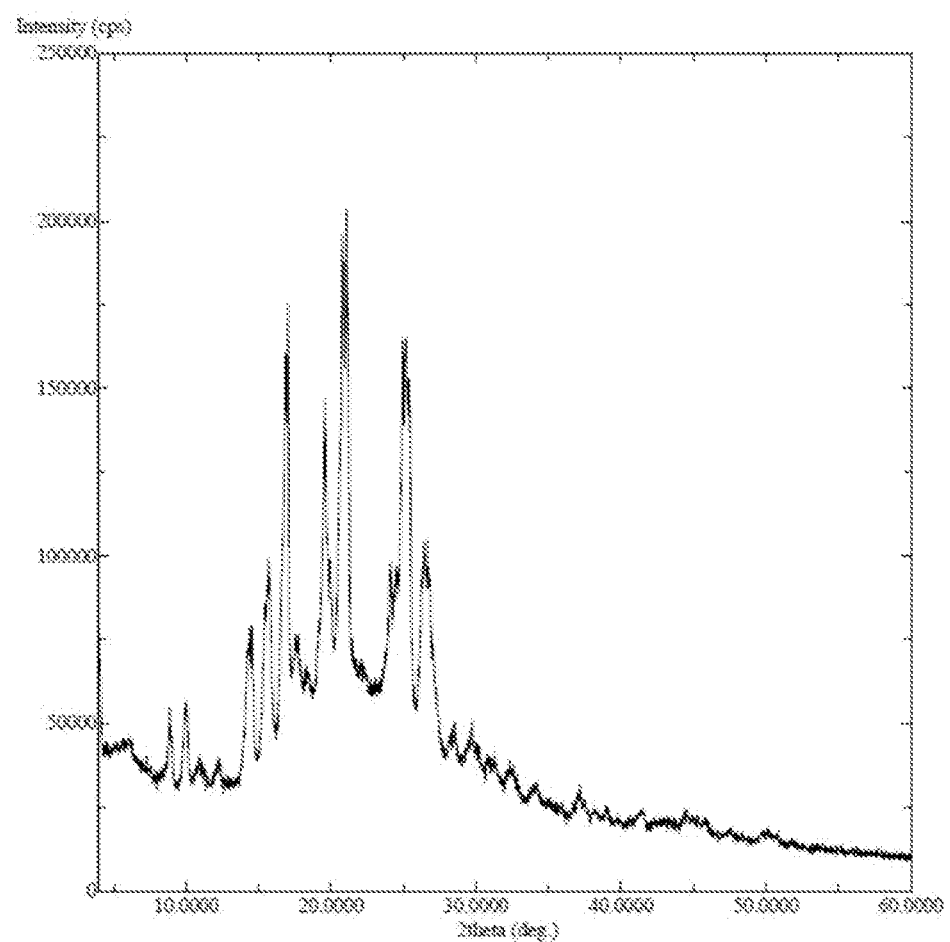
FIG. 7: PXRD of (E)-N-{4-[3-chloro-4-(2-pyridinylmethoxy)aniline]-3-cyano-7-ethoxy-6-quinolinyl}-4-(dimethylamino)-2-butenamide citrate salt.
Figure 8:
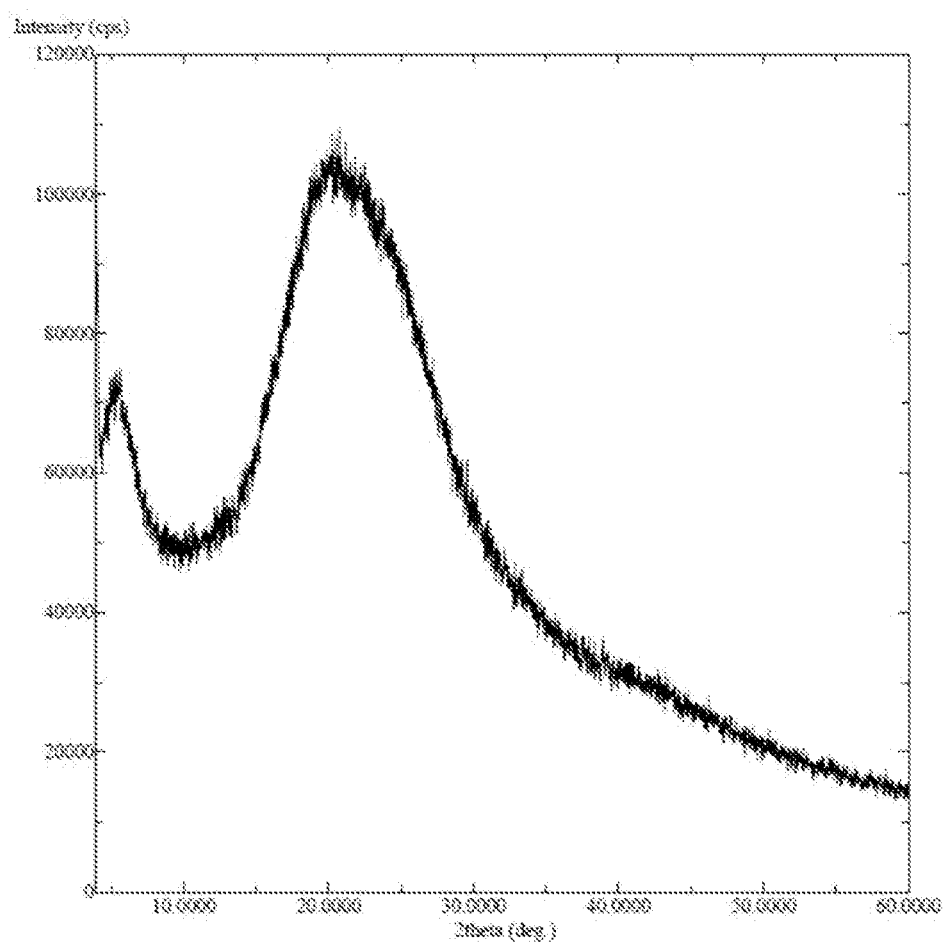
FIG. 8: PXRD of (E)-N-{4-[3-chloro-4-(2-pyridinylmethoxy)aniline]-3-cyano-7-ethoxy-6-quinolinyl}-4-(dimethylamino)-2-butenamide L-malate salt.
Figure 9:
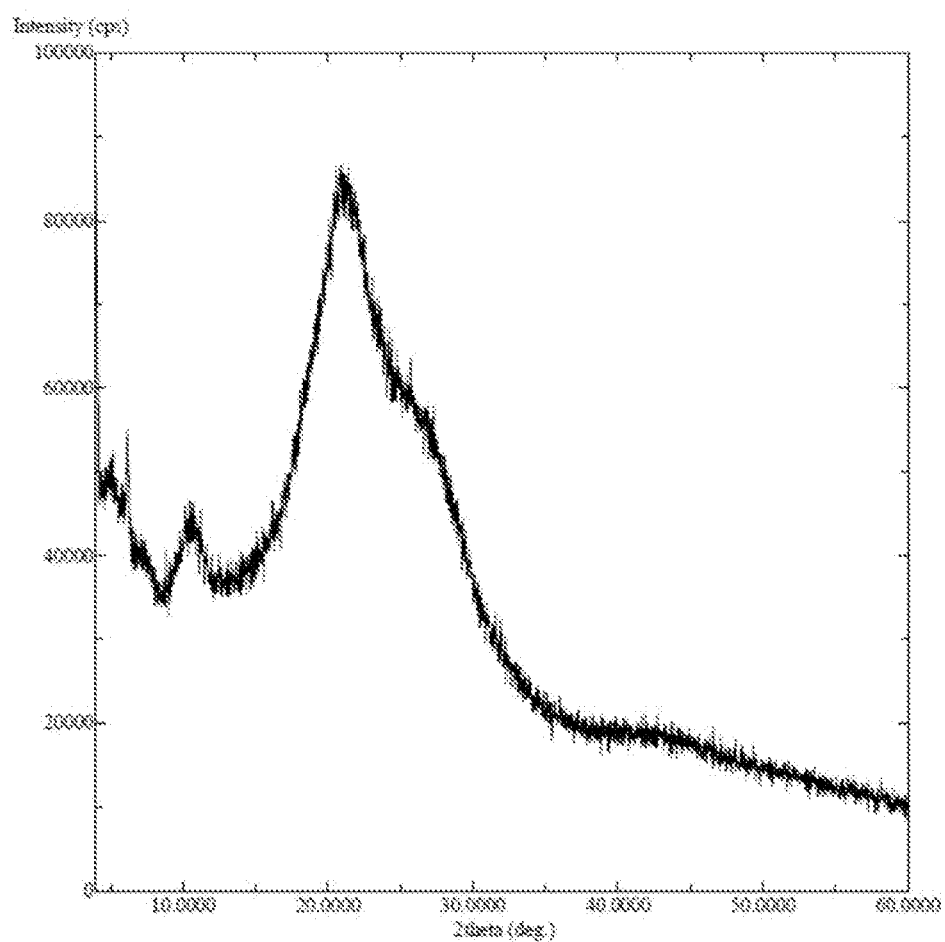
FIG. 9: PXRD of (E)-N-{4-[3-chloro-4-(2-pyridinyl-methoxy)aniline]-3-cyano-7-ethoxy-6-quinolinyl}-4-(dimethylamino)-2-butenamide sulphate salt.

| Salt | Crystallinity by PXRD | PXRD pattern |
|---|---|---|
| Hydrochloride acid salt | amorphous | FIG. 6 |
| Citrate salt | crystalline | FIG. 7 |
| L-malate salt | amorphous | FIG. 8 |
| Sulphate salt | amorphous | FIG. 9 |
| Maleate salt | crytalline | FIG. 3 |

Bioavailability of ((E)-N-(3-cyano-7-ethoxy-4-((4-phenoxyphenyl)amino)quinolin-6-yl)-4-(dimethylamino)but-2-enamide in maleate and citrate salt has been tested. SD rats (240-250 g, male, N=6; purchased from Sino-British SIPPR/BK Lab Animal Ltd, Shanghai, China) were administrated by I.V.: 5 mg/kg (5 mL/kg) via foot dorsal vein injection (N=3), PO: 10 mg/kg (10 mL/kg) via gavage (N=3); and the blood samples of the animals were collected at the designated time points (predose, 0.0833 h, 0.25 h, 0.5 h, 1 h, 2 h, 4 h, 8 h, 24 h). The bioavailability of maleate and citrate are respectively 49.6% and 36.7%.

The above results has shown that ((E)-N-(3-cyano-7-ethoxy-4-((4-phenoxyphenyl) amino)quinolin-6-yl)-4-(dimethylamino)but-2-enamide in maleate has more excellent physiochemical properties and better bioavailability than other salts, which are unexpectable by a person skilled in the art.

Instrument and Method

PXRD is performed in Rigaku UltimaIV diffractometer, copper target, λ=1.5406 A; working voltage 40 kv; working current: 40 Ma; scan speed: 60.000 deg./min; scan range: 4.0000->60.0000 deg.

Differential Scanning Calorimetry (DSC) is performed in US TA Q2000, and TGA in US TA Q2000.

FT-IR spectra were performed by using a Fourier transform infrared spectrophotometer, and potassium bromide (KBr) pellet.

Meanwhile, the following compounds and their salts such as sulphate, hydrochloride, L-malate, citrate, and maleate have been contemplated according to WO2013152135:
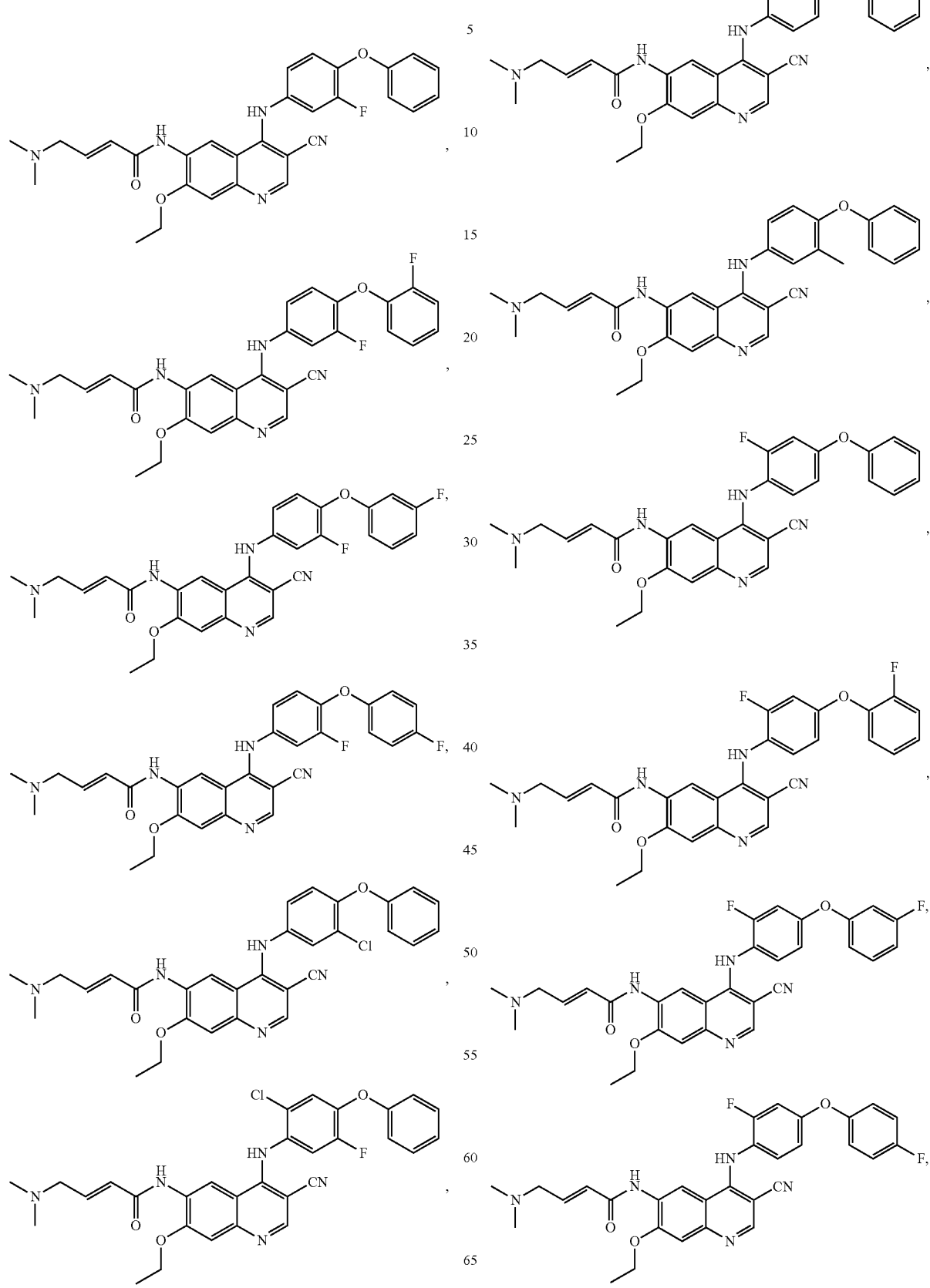

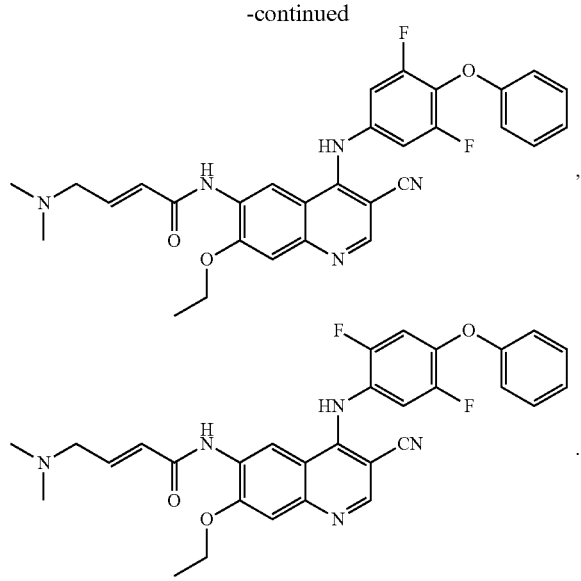

Synthesis and Preparation

Example 1. (E)-N-(3-cyano-7-ethoxy-4-((4-phenoxyphenyl)amino)quinolin-6-yl)-4-(dimethylamino)but-2-enamide Sulfate

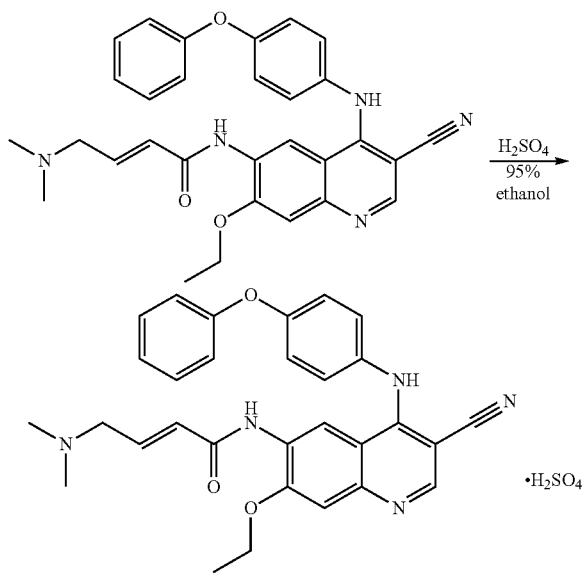

95% ethanol (4.0 ml) was added to (E)-N-(3-cyano-7-ethoxy-4-((4-phenoxyphenyl)amino) quinolin-6-yl)-4-(dimethylamino)but-2-enamide (500 mg, 0.99 mmol, 1.0 eq), followed sulfuric acid (101.9 mg, 1.04 mmol, 1.05 eq) in 95% ethanol (1.0 ml) was added dropwise to the reaction mixture. Then an amount of precipitate was founded. Another 95% (60 ml) was added to the reaction mixture and the reaction mixture was heated to 70° C. Filtered and the filtrate was heated to 70° C. again. Then the reaction mixture was cooled to room temperature and The reaction mixture was crystallized at −10° C. for 41.5 h. Filtered the precipitated solid and dried at 40° C. under vacuum for 1 hour to get the title compound (260 mg) as a yellow solid.

X-ray detection shows an amorphous structure to the compound as FIG. 9.

Example 2. Synthesis of (E)-N-(3-cyano-7-ethoxy-4-((4-phenoxyphenyl)amino) quinolin-6-yl)-4-(dimethylamino)but-2-enamide Hydrochloride

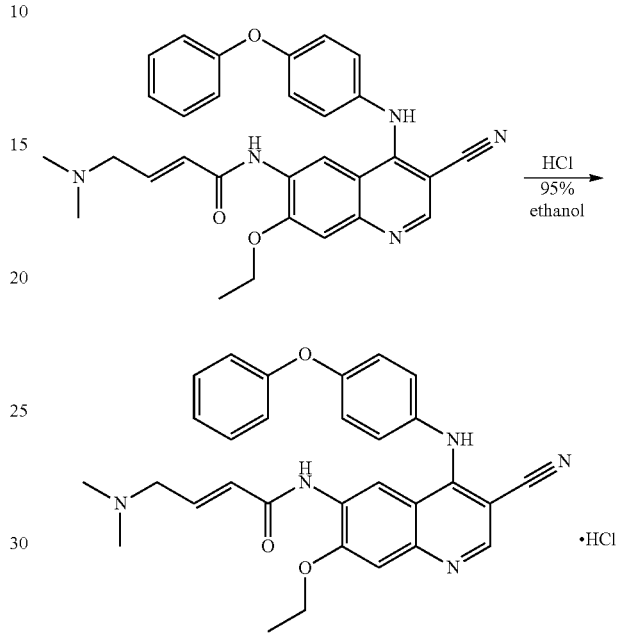

95% ethanol (5.0 ml) was added to (E)-N-(3-cyano-7-ethoxy-4-((4-phenoxyphenyl) amino)quinolin-6-yl)-4-(dimethylamino)but-2-enamide (500 mg, 0.99 mmol, 1.0 eq), followed hydrochloric acid (38.0 mg, 1.04 mmol, 1.05 eq) in 95% ethanol (1.0 ml) was added dropwise to the reaction mixture. The reaction mixture was heated to 70° C. Filtered and the filtrate was crystallized under −10° C. for 44.5 h. Filtered the precipitated solid and dried at 40° C. under vacuum for 1 hour to get the title compound (96 mg) as a yellow solid.

X-ray detection shows an amorphous structure to the compound in FIG. 6.

Example 3. Synthesis of (E)-N-(3-cyano-7-ethoxy-4-((4-phenoxyphenyl)amino) quinolin-6-yl)-4-(dimethylamino)but-2-enamide Malate

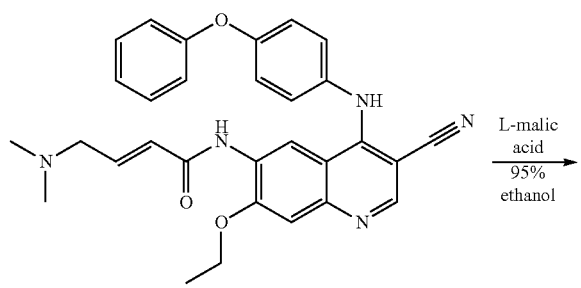

-continued

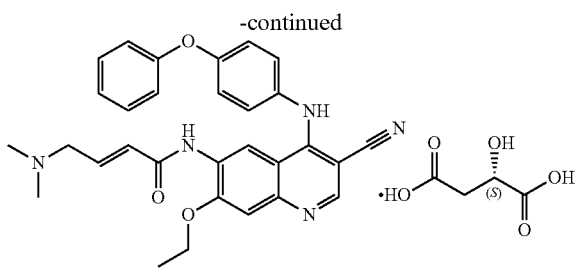

(E)-N-(3-cyano-7-ethoxy-4-((4-phenoxyphenyl)amino)quinolin-6-yl)-4-(dimethylamino)but-2-enamide (500 mg, 0.99 mmol, 1.0 eq), L-malic acid (139.4 mg, 1.04 mmol, 1.05 eq) and 95% ethanol (5.0 ml) was added to a 50 ml round-bottom flask. The reaction mixture was heated to 70° C. Filtered and the filtrate was crystallized under −10° C. for 45.5 h. A little of precipitate was founded and then the reaction mixture was evaporated under vacuum at 40° C. to give the target (370 mg) as a yellow solid.

X-ray detection shows an amorphous structure to the compound in FIG. 8

Example 4: Synthesis of (E)-N-(3-cyano-7-ethoxy-4-((4-phenoxyphenyl)amino)quinolin-6-yl)-4-(dimethylamino)but-2-enamide Citrate

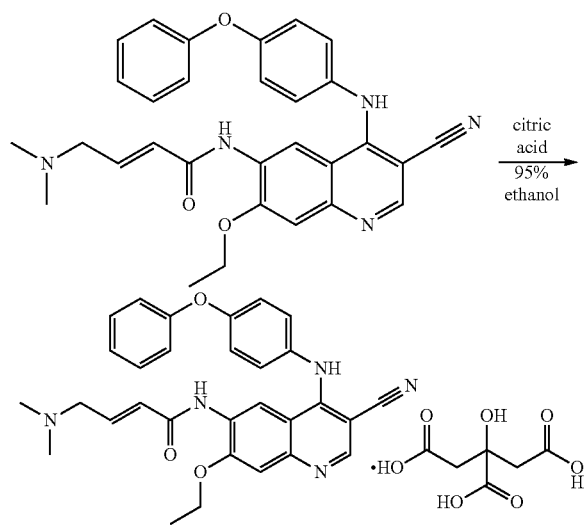

To a solution of (E)-N-(3-cyano-7-ethoxy-4-((4-phenoxyphenyl) amino)quinolin-6-yl)-4-(dimethylamino)but-2-enamide (500 mg, 0.99 mmol, 1.0 eq), citric acid (198.8 mg, 1.04 mmol, 1.05 eq) and 95% ethanol (5.0 ml). The reaction mixture was heated to 70° C. Filtered and the filtrate was crystallized under −10° C. for 45 h. A little of precipitate was founded and then the reaction mixture was evaporated under vacuum at 40° C. to give the target compound (610 mg) as a yellow solid.

X-ray detection shows an crystalline structure to the compound in FIG. 7.

Example 5: Preparation of (E)-N-(3-cyano-7-ethoxy-4-((4-phenoxyphenyl)amino) quinolin-6-yl)-4-(dimethylamino)but-2-enamide Maleate Monohydrate (E)-N-(3-cyano-7-ethoxy-4-((4-phenoxyphenyl)amino)quinolin-6-yl)-4-(dimethylamino)but-2-enamide free base (0.091 kg) is rinsed with a 10% solution of USP purified water in n-propanol (0.082 kg, 0.10 L) followed by the addition of water:n-propanol solution (0.74 kg, 0.90 L). Maleic acid is added (1.01 equiv) and the mixture is rinsed with 10% water:n-propanol (0.082 kg, 0.10 L). The mixture is quickly heated to 50-60° C. and held for a minimum of 15 min. until a solution is obtained. The hot solution is clarified through a pre-heated 50-60° C., 0.2 Mm filter cartridge and the filtrates are collected in a preheated 45-55° C., 2 L multi-neck flask. The filter cartridge is rinsed through with 10% water:n-propanol pre-heated to 45-55° C. (0.082 kg, 0.10 L). The solution is cooled over at least one hour to 40° C. and held at that temperature for 12 hours then cooled to room temperature (25° C.) over a minimum of four hours and held at that temperature for at least two hours. The mixture is filtered on a 12.5 cm diameter Buchner funnel for 5 min., then rinsed and washed with prefiltered 10% water:n-propanol solution (2×0.12 kg, 2×0.15 L). The cake is dammed and suction maintained until dripping essentially stops, about 1 h.

PXRD is shown in FIG. 1.

Example 6

The product from Example 1 is dried (50° C., 10 mm Hg, 24 h) to give crystalline, anhydrous (E)-N-(3-cyano-7-ethoxy-4-((4-phenoxyphenyl)amino)quinolin-6-yl)-4-(dimethylamino)but-2-enamide maleate.

PXRD is shown in FIG. 3.

Example 7: Preparation of (E)-N-(3-cyano-7-ethoxy-4-((4-phenoxyphenyl) amino)quinolin-6-yl)-4-(dimethylamino)but-2-enamide Maleate Monohydrate To a solution of (E)-N-(3-cyano-7-ethoxy-4-((4-phenoxyphenyl)amino)quinolin-6-yl)-4-(dimethylamino)but-2-enamide (38.0 g, 75.0 mmol, 1.0 eq) and n-propanol/H$_2$O (380 ml, V:V=9:1). maleic acid (8.7 g, 75.0 mmol, 1.0 eq) in n-propanol/H$_2$O (76 ml, V:V=9:1) was added to the reaction mixture. An amount of precipitate was founded, then the reaction mixture was heated to 65° C. The solid was dissolved completely, then the reaction mixture was cooled to room temperature and stand for 20 hours. Filtered and filtrate was evaporated under vacuum to get the crude product.

The crude product (14.0 g) was recrystallized in n-propanol/H$_2$O (240 ml, V:V=9:1) at 70° C. The solid was dissolved completely, then the reaction mixture was cooled to room temperature and stand for 20.5 hours. Filtered and wash the cake with n-propanol/H$_2$O (20 ml, V:V=9:1) to get target product (12.9 g, wet).

PXRD as FIG. 1.

Example 8: Crystalline, Anhydrous (E)-N-(3-cyano-7-ethoxy-4-((4-phenoxyphenyl) amino)quinolin-6-yl)-4-(dimethylamino)but-2-enamide Maleate To a solution of (E)-N-(3-cyano-7-ethoxy-4-((4-phenoxyphenyl)amino)quinolin-6-yl)-4-(dimethylamino)but-2-enamide (21.5 g, 42.4 mmol, 1.0 eq) and ethanol (300 ml). maleic acid (5.2 g, 44.8 mmol, 1.05 eq) was added to the reaction mixture. An amount of precipitate was founded, then the reaction mixture was heated to 70° C. Another ethanol (1980 ml) was added to the reaction mixture in several times and the reaction temperature was keep at 70° C. Filtered and filtrate was cooled to room temperature, stop stirring and stand for 16-20 hours. Filtered and the solid was dried at room temperature for 24 hours to get the title compound.

PXRD as FIG. 3.

The invention claimed is:

1. A crystalline form of maleate salt of (E)-N-(3-cyano-7-ethoxy-4-((4-phenoxyphenyl)amino)quinolin-6-yl)-4-(dimethylamino)but-2-enamide, exhibiting:
   (a) a first X-ray powder diffraction pattern comprising peaks of 2-theta angles of about 8.1, 15.0, 17.6, and 23.6 degrees; or
   (b) a second X-ray powder diffraction pattern comprising peaks of 2-theta angles of about 15.5, 16.8, 20.9, 24.4, 25.2 and 26.5 degrees.

2. The crystalline form of claim 1, wherein the first X-ray powder diffraction pattern further comprises peaks of 2-theta angles of about 9.0, 18.5, 22.7, 23.0, and 25.1 degrees.

3. The crystalline form of claim 1, wherein the second X-ray powder diffraction pattern further comprises peaks of 2-theta angles of about 8.7, 9.8, 14.3, 17.4, 19.3, 19.8, and 23.8 degrees.

4. The crystalline form of claim 1, which is characterized as: an anhydrous form, a monohydrate form, or a mixture of the anhydrous and the monohydrate forms.

5. The crystalline form of claim 1, wherein the first X-ray powder diffraction pattern is essentially the same as shown in FIG. 3.

6. The crystalline form of claim 1, wherein the second X-ray powder diffraction pattern is essentially the same as shown in FIG. 1.

7. The crystalline form of claim 1, wherein the crystalline form exhibits the second X-ray powder diffraction pattern and a differential scanning calorimetry (DSC) thermogram having two endothermic peaks between 153° C. and 180° C.

8. The crystalline form claim 1, wherein the crystalline form exhibits the second X-ray powder diffraction pattern and an infrared spectroscopy (IR) spectra comprising one or more peaks at about 3507.20, 3326.14, 3036.83, 2995.35, 2938.83, 2640.50, 2417.18, 2214.77, 1847.62, 1686.72, 1620.70, 1581.83, 1539.15, 1485.39, 1459.27, 1386.91, 1349.85, 1278.17, 1226.56, 1163.32, 1113.32, 1078.80, 1034.16, 979.59, 866.53, 829.88, 747.82, 700.14, 662.23, 556.48, and 487.55 cm$^{-1}$.

9. A method for preparing the crystalline form of claim 1, comprising: mixing ((E)-N-(3-cyano-7-ethoxy-4-((4-phenoxyphenyl) amino)quinolin-6-yl)-4-(dimethylamino)but-2-enamide and maleic acid in a water-alcohol solution or an alcohol solution at an elevated temperature.

10. The method of claim 9, further comprising: cooling said water-alcohol solution or said alcohol solution to precipitate said crystalline form; and filtering said water-alcohol solution or said alcohol solution after cooling to obtain crystalline (E)-N-(3-cyano-7-ethoxy-4-((4-phenoxyphenyl)amino)quinolin-6-yl)-4-(dimethylamino)but-2-enamide maleate.

11. A pharmaceutical composition comprising the crystalline form of claim 1 and a pharmaceutically acceptable carrier.

12. A method for treating or inhibiting cancer comprising, administering to a subject a therapeutically-effective amount of the crystalline form of claim 1.

13. The method according to claim 12, wherein said cancer is selected from at least one of: breast cancer, ovarian cancer, epidermoid tumors, colon cancer, prostate cancer, kidney cancer, bladder cancer, larynx cancer, esophagus cancer, stomach cancer, lung cancer, chronic lymphocytic leukemia, mantle cell lymphoma, diffuse large B-cell lymphoma, and multiple myeloma.

14. The crystalline form of claim 7, wherein the differential scanning calorimetry (DSC) thermogram of the crystalline form is substantially as shown in FIG. 2.

15. The pharmaceutical composition of claim 11, wherein the crystalline form is characterized as: an anhydrous form, a monohydrate form, or a mixture of the anhydrous and the monohydrate forms.

16. The method of claim 9, wherein the water-alcohol solution is a water and n-propanol solution, and wherein the alcohol solution is an ethanol solution.

17. The method of claim 16, wherein the elevated temperature is about 70° C.

18. A process for preparing the crystalline form of claim 1, comprising:
   (a) dissolving (E)-N-(3-cyano-7-ethoxy-4-((4-phenoxyphenyl)amino)quinolin-6-yl)-4-(dimethylamino)but-2-enamid and maleic acid in a water-alcohol solution at a first elevated temperature;
   (b) filtering, at a second elevated temperature, the water-alcohol solution obtained in (a) to provide a filtrate;
   (c) cooling the filtrate obtained in (b) to a third elevated temperature; and
   (d) further cooling the filtrate to about 25° C. and isolating the crystalline form of claim 1.

19. The process of claim 18, wherein the first elevated temperature is from 50° C. to 60° C.; the second elevated temperature is from 45° C. to 55° C.; and the third elevated temperature is about 40° C.

20. The process of claim 18, wherein the crystalline form of claim 1 exhibits the second X-ray powder diffraction pattern.

* * * * *